(12) United States Patent
Veyland et al.

(10) Patent No.: US 8,754,164 B2
(45) Date of Patent: Jun. 17, 2014

(54) RUBBER COMPOSITION COMPRISING A 1,2,4-TRIAZINE

(75) Inventors: Anne Veyland, Marsat (FR); Nicolas Seeboth, Clermont-Ferrand (FR); Jose Carlos Araujo Da Silva, Pont du Chateau (FR)

(73) Assignees: Compagnie Generale des Etablissements Michelin, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 54 days.

(21) Appl. No.: 13/501,083

(22) PCT Filed: Oct. 8, 2010

(86) PCT No.: PCT/EP2010/065069
§ 371 (c)(1),
(2), (4) Date: Sep. 25, 2012

(87) PCT Pub. No.: WO2011/042522
PCT Pub. Date: Apr. 14, 2011

(65) Prior Publication Data
US 2013/0053509 A1 Feb. 28, 2013

(30) Foreign Application Priority Data

Oct. 8, 2009 (FR) ..................... 09 57037

(51) Int. Cl.
| C08K 3/04 | (2006.01) |
| C08K 5/3462 | (2006.01) |
| C07D 211/94 | (2006.01) |
| C07D 211/46 | (2006.01) |
| C08K 5/548 | (2006.01) |
| C08F 8/32 | (2006.01) |

(52) U.S. Cl.
USPC ........ 524/575.5; 524/100; 524/102; 524/103; 524/571; 525/375

(58) Field of Classification Search
CPC ...... C08K 5/0025; C08K 5/3492; C08K 5/43; C08L 21/00; B60C 1/00; B60C 1/0016; C07D 253/07
USPC .......... 524/182, 322, 100–103, 571; 525/375, 525/575.5
See application file for complete search history.

(56) References Cited

U.S. PATENT DOCUMENTS

| 3,655,599 A | 4/1972 | Kay et al. |
| 5,891,938 A * | 4/1999 | Williams ...................... 524/100 |
| 2013/0053559 A1* | 2/2013 | Seeboth et al. ............... 544/182 |

FOREIGN PATENT DOCUMENTS

| EP | 2141164 | * | 7/2008 |
| GB | 1095219 | | 12/1967 |

* cited by examiner

*Primary Examiner* — Liam Heincer
*Assistant Examiner* — Marilou Lacap
(74) *Attorney, Agent, or Firm* — Cozen O'Connor

(57) ABSTRACT

A rubber composition for the manufacture of tires, based on one or more diene elastomers, on one or more reinforcing fillers and on a vulcanization system, characterized in that the said vulcanization system comprises one or more 1,2,4-triazine compounds of formula:

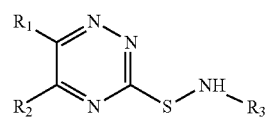

(I)

16 Claims, No Drawings

RUBBER COMPOSITION COMPRISING A 1,2,4-TRIAZINE

RELATED APPLICATIONS

This is a U.S. national stage of application No. PCT/EP2010/065069, filed on Oct. 8, 2010. Priority is claimed on the following application: French Application No.: 0957037 filed on Oct. 8, 2009, the disclosure content of which is hereby incorporated here by reference.

FIELD OF THE INVENTION

The present invention relates to a rubber composition which can be used in particular in the manufacture of tires or semi-finished products for tires, such as treads, the said composition being based on a diene elastomer, on a reinforcing filler and on a vulcanization system comprising a specific 1,2,4-triazine compound.

BACKGROUND OF THE INVENTION

The vulcanization of diene elastomers by sulphur is widely used in the rubber industry, in particular in the tire industry. Use is made, to vulcanize diene elastomers, of a relatively complex vulcanization system comprising, in addition to sulphur, a primary vulcanization accelerator, such as sulphenamides comprising a benzothiazole ring system, and various secondary vulcanization accelerators or vulcanization activators, very particularly zinc derivatives, such as zinc oxide (ZnO), alone or used with fatty acids.

The sulphenamides comprising a benzothiazole ring system used as primary vulcanization accelerators are, for example, N-cyclohexyl-2-benzothiazolesulphenamide (abbreviated to "CBS"), N,N-dicyclohexyl-2-benzothiazolesulphenamide (abbreviated to "DCBS"), N-tert-butyl-2-benzothiazolesulphenamide (abbreviated to "TBBS") and the mixtures of these compounds.

Vulcanization accelerators play an important role in the achievement of a delay phase (induction period), that is to say the time necessary for the start of the vulcanization reaction, and it is known to a person skilled in the art that this parameter is very difficult to adjust. It is therefore particularly advantageous for a person skilled in the art to have a vulcanization accelerator which induces a lengthy delay phase, which he can adjust, if desired, by the addition of supplementary accelerators.

SUMMARY OF THE INVENTION

The inventors have discovered novel rubber compositions which can be used in particular for the manufacture of tires, in particular of treads, based on diene elastomers, on reinforcing fillers and on a vulcanization system exhibiting a satisfactory cross-linking while having a longer delay phase, while retaining the normal properties of rubber compositions.

One aspect of the invention is directed to a rubber composition for the manufacture of tires, based on one or more diene elastomers, on one or more reinforcing fillers and on a vulcanization system, the vulcanization system comprising one or more 1,2,4 triazine compounds of formula:

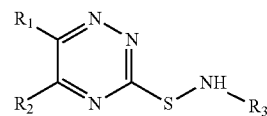

(I)

where $R_1$ and $R_2$ independently represent H or a $C_1$-$C_{25}$-hydrocarbon group chosen from linear, branched or cyclic alkyl groups and aryl groups, optionally interrupted by one or more heteroatoms, it being possible for $R_1$ and $R_2$ to together form a ring, $R_3$ represents:
  a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
  a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

Another aspect of the invention is directed to a process for preparing a rubber composition for the manufacture of tires as defined in any one of the preceding claims, characterized in that it comprises the following stages:
  incorporating the reinforcing filler or fillers in the diene elastomer or elastomers, during a first "non-productive" stage, everything being kneaded thermomechanically, in one or more goes, until a maximum temperature of between 130° C. and 200° C. is reached,
  cooling the combined mixture to a temperature of less than 100° C.,
  subsequently incorporating, during a second "productive" stage, the vulcanization system and then
  kneading everything up to a maximum temperature of less than 120° C.

Another aspect of the invention is directed to the use of a composition according to an embodiment of the invention in the manufacture of a finished article or a semi-finished product intended for a motor vehicle ground-contact system, such as tire, internal tire safety support, wheel, rubber spring, elastomeric joint or other suspension and anti-vibratory element. In particular, the composition according to the invention can be used in the manufacture of semi-finished rubber products intended for tires, such as treads, crown reinforcing plies, sidewalls, carcass reinforcing plies, beads, protectors, underlayers, rubber blocks and other internal rubbers, in particular decoupling rubbers, intended to provide the bonding or the interface between the above-mentioned regions of the tires.

A further aspect of the invention is a finished article or semi-finished product intended for a motor vehicle ground-contact system, in particular the tires and semi-finished products for tires comprising a composition according to an embodiment of the invention. The tires in accordance with the invention are intended in particular for passenger vehicles as for industrial vehicles chosen from vans, heavy-duty vehicles—i.e., underground, bus, heavy road transport vehicles (lorries, tractors, trailers) or off-road vehicles—, agricultural vehicles or earth-moving equipment, aircraft, or other transportation or handling vehicles.

A final aspect of the invention is the use as vulcanization accelerator, in a composition based on one or more diene elastomers, on one or more reinforcing fillers and on a vulcanization system, of one or more 1,2,4 triazine compounds of formula (I).

DETAILED DISCUSSION

The invention and its advantages will be easily understood in the light of the description and implementation examples which follow.

I. Measurements and Tests Used

The rubber compositions, in which the 1,2,4-triazine vulcanization accelerators are tested, are characterized, before and after curing, as indicated below.

Mooney Plasticity

Use is made of an oscillating consistometer as described in French Standard NF T 43-005 (1991). The Mooney plasticity measurement is carried out according to the following principle: the composition in the raw state (i.e., before curing) is moulded in a cylindrical chamber heated to 100° C. After preheating for one minute, the rotor rotates within the test specimen at 2 revolutions/minute and the working torque for maintaining this movement is measured after rotating for 4 minutes. The Mooney plasticity (ML 1+4) is expressed in "Mooney unit" (UM, with 1 UM=0.83 newton.meter).

Rheometry

The measurements are carried out at 150° C. with an oscillating disc rheometer, according to Standard DIN 53529—part 3 (June 1983). The change in the rheometric torque, $\Delta$Torque, as a function of time describes the change in the stiffening of the composition as a result of the vulcanization reaction. The measurements are processed according to Standard DIN 53529—part 2 (March 1983): $t_0$ is the induction period, that is to say the time necessary for the start of the vulcanization reaction; $t_\alpha$ (for example $t_{99}$) is the time necessary to achieve a conversion of $\alpha$%, that is to say $\alpha$% (for example 99%) of the difference between the minimum and maximum torques. The conversion rate constant, denoted K (expressed in $\min^{-1}$), which is 1st order, calculated between 30% and 80% conversion, which makes it possible to assess the vulcanization kinetics, is also measured.

Tensile Tests

These tensile tests make it possible to determine the elasticity stresses and the properties at break. Unless otherwise indicated, they are carried out in accordance with French Standard NF T 46-002 of September 1988. The nominal secant modulus (or apparent stress, in MPa) is measured in second elongation (i.e., after an accommodation cycle at the degree of extension planned for the measurement itself) at 10% elongation (denoted MA10), at 100% elongation (denoted MA 100) and at 300% elongation (denoted MA 300).

The breaking stresses (in MPa) and elongations at break (in %) are also measured. All these tensile measurements are carried out at a temperature of 100° C.±2° C. and under standard hygrometric conditions (50±5% relative humidity), according to French standard NF T 40-101 (December 1979).

Dynamic Properties

The dynamic properties, $\Delta G^*$ and $\tan(\delta)_{max}$, are measured on a viscosity analyser (Metravib VA4000), according to Standard ASTM D 5992-96. The response of a sample of vulcanized composition (cylindrical test specimen with a thickness of 4 mm and with a cross section of 400 $mm^2$), subjected to a simple alternating sinusoidal shear stress, at a frequency of 10 Hz, under standard temperature conditions (23° C.) according to Standard ASTM D 1349-99 or, as the case may be, at a different temperature, is recorded. A strain amplitude sweep is carried out from 0.1% to 45% (outward cycle) and then from 45% to 0.1% (return cycle). The results made use of are the complex dynamic shear modulus ($G^*$) and the loss factor, $\tan(\delta)$. The maximum value of $\tan(\delta)$ observed, denoted $\tan(\delta)_{max}$, and the difference in complex modulus ($\Delta G^*$) between the values at 0.1% and at 45% strain (Payne effect) are shown for the return cycle.

II. Conditions for the Implementation of the Invention

As explained above, the composition according to the invention is based on one or more diene elastomers, on one or more reinforcing fillers and on a vulcanization system.

The expression composition "based on" should be understood as meaning a composition comprising the mixture and/or the reaction product of the various constituents used, some of these base constituents being capable of reacting or intended to react with one another, at least in part, during the various phases of manufacture of the composition, in particular during its vulcanization.

In the present description, unless expressly indicated otherwise, all the percentages (%) are % by weight. Moreover, any interval of values denoted by the expression "between a and b" represents the range of values extending from greater than a to less than b (i.e., limits a and b excluded), whereas any interval of values denoted by the expression "from a to b" means the range of values extending from a up to b (i.e., including the strict limits a and b).

II-1. Diene Elastomer

The term "diene" elastomer or rubber should be understood as meaning, in a known way, an elastomer resulting at least in part (i.e., a homopolymer or a copolymer) from diene monomers (monomers carrying two carbon-carbon double bonds which may or may not be conjugated).

These diene elastomers can be classified into two categories: "essentially unsaturated" or "essentially saturated". The term "essentially unsaturated" is understood to mean generally a diene elastomer resulting at least in part from conjugated diene monomers having a level of units of diene origin (conjugated dienes) which is greater than 15% (molar %); thus it is that diene elastomers such as butyl rubbers or copolymers of dienes and of $\alpha$-olefins of EPDM type do not come within the preceding definition and can in particular be described as "essentially saturated" diene elastomers (low or very low level of units of diene origin, always less than 15%). In the category of "essentially unsaturated" diene elastomers, the term "highly unsaturated" diene elastomer is understood to mean in particular a diene elastomer having a level of units of diene origin (conjugated dienes) which is greater than 50%.

Given these definitions, the term diene elastomer capable of being used in the compositions in accordance with the invention is understood more particularly to mean:

(a)—any homopolymer obtained by polymerization of a conjugated diene monomer having from 4 to 12 carbon atoms;
(b)—any copolymer obtained by copolymerization of one or more conjugated dienes with one another or with one or more vinylaromatic compounds having from 8 to 20 carbon atoms;
(c)—a ternary copolymer obtained by copolymerization of ethylene and of an $\alpha$-olefin having from 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;

(d)—a copolymer of isobutene and of isoprene (butyl rubber) and also the halogenated versions, in particular chlorinated or brominated versions, of this type of copolymer.

Although it applies to any type of diene elastomer, a person skilled in the art of tires will understand that the present invention is preferably employed with essentially unsaturated diene elastomers, in particular of the type (a) or (b) above.

The following are suitable in particular as conjugated dienes: 1,3-butadiene, 2-methyl-1,3-butadiene, 2,3-di($C_1$-$C_5$ alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-isopropyl-1,3-butadiene, an aryl-1,3-butadiene, 1,3-pentadiene or 2,4-hexadiene. The following, for example, are suitable as vinylaromatic compounds: stirene, ortho-, meta- or para-methylstirene, the "vinyltoluene" commercial mixture, para-(tert-butyl)stirene, methoxystirenes, chlorostirenes, vinylmesitylene, divinylbenzene or vinylnaphthalene.

The copolymers can comprise between 99% and 20% by weight of diene units and between 1% and 80% by weight of vinylaromatic units. The elastomers can have any microstructure which depends on the polymerization conditions used, in particular on the presence or absence of a modifying and/or randomizing agent and on the amounts of modifying and/or randomizing agent employed. The elastomers can, for example, be block, random, sequential or microsequential elastomers and can be prepared in dispersion, in emulsion or in solution; they can be coupled and/or star-branched or also functionalized with a coupling and/or star-branching or functionalization agent. For coupling with carbon black, mention may be made, for example, of functional groups comprising a C—Sn bond or of aminated functional groups, such as aminobenzophenone, for example; for coupling with a reinforcing inorganic filler, such as silica, mention may be made, for example, of silanol functional groups or polysiloxane functional groups having a silanol end (such as described, for example, in FR 2 740 778, U.S. Pat. No. 6,013,718 or WO 2008/141702), of alkoxysilane groups (such as described, for example, in FR 2 765 882 or U.S. Pat. No. 5,977,238), of carboxyl groups (such as described, for example, in WO 01/92402, U.S. Pat. No. 6,815,473, WO 2004/096865 or US 2006/0089445) or of polyether groups (such as described, for example, in EP 1 127 909, U.S. Pat. No. 6,503,973, WO 2009/000750 or WO 2009/000752). Mention may also be made, as other examples of functionalized elastomers, of elastomers (such as SBR, BR, NR or IR) of the epoxidized type.

The following are suitable: polybutadienes, in particular those having a content (molar %) of 1,2-units of between 4% and 80% or those having a content (molar %) of cis-1,4-units of greater than 80%, polyisoprenes, butadiene/stirene copolymers and in particular those having a Tg (glass transition temperature, measured according to ASTM D3418) of between 0° C. and −70° C. and more particularly between −10° C. and −60° C., a stirene content of between 5% and 60% by weight and more particularly between 20% and 50%, a content (molar %) of 1,2-bonds of the butadiene part of between 4% and 75% and a content (molar %) of trans-1,4-bonds of between 10% and 80%, butadiene/isoprene copolymers, in particular those having an isoprene content of between 5% and 90% by weight and a Tg of −40° C. to −80° C., or isoprene/stirene copolymers, in particular those having a stirene content of between 5% and 50% by weight and a Tg of between 5° C. and −50° C. In the case of butadiene/stirene/isoprene copolymers, those having a stirene content of between 5% and 50% by weight and more particularly of between 10% and 40%, an isoprene content of between 15% and 60% by weight and more particularly of between 20% and 50%, a butadiene content of between 5% and 50% by weight and more particularly of between 20% and 40%, a content (molar %) of 1,2-units of the butadiene part of between 4% and 85%, a content (molar %) of trans-1,4-units of the butadiene part of between 6% and 80%, a content (molar %) of 1,2-plus 3,4-units of the isoprene part of between 5% and 70% and a content (molar %) of trans-1,4-units of the isoprene part of between 10% and 50%, and more generally any butadiene/stirene/isoprene copolymer having a Tg of between −5° C. and −70° C., are suitable in particular.

To sum up, the diene elastomer or elastomers of the composition according to the invention are preferably chosen from the group of the highly unsaturated diene elastomers consisting of polybutadienes (abbreviated to "BR"), synthetic polyisoprenes (IR), natural rubber (NR), butadiene copolymers, isoprene copolymers and the mixtures of these elastomers. Such copolymers are more preferably chosen from the group consisting of butadiene/stirene copolymers (SBR), isoprene/butadiene copolymers (BIR), isoprene/stirene copolymers (SIR) and isoprene/butadiene/stirene copolymers (SBIR).

According to a specific embodiment, the diene elastomer is predominantly (i.e., for more than 50 phr) an SBR, whether an SBR prepared in emulsion ("ESBR") or an SBR prepared in solution ("SSBR"), or an SBR/BR, SBR/NR (or SBR/IR), BR/NR (or BR/IR) or also SBR/BR/NR (or SBR/BR/IR) blend (mixture). In the case of an SBR (ESBR or SSBR) elastomer, use is made in particular of an SBR having a moderate stirene content, for example of between 20% and 35% by weight, or a high stirene content, for example from 35% to 45%, a content of vinyl bonds of the butadiene part of between 15% and 70%, a content (molar %) of trans-1,4-bonds of between 15% and 75% and a Tg of between −10° C. and −55° C.; such an SBR can advantageously be used as a mixture with a BR preferably having more than 90% (molar %) of cis-1,4-bonds.

According to another specific embodiment, the diene elastomer is predominantly (for more than 50 phr) an isoprene elastomer. This is the case in particular when the compositions of the invention are intended to constitute, in the tires, rubber matrices of certain treads (for example for industrial vehicles), of crown reinforcing plies (for example of working plies, protection plies or hooping plies), of carcass reinforcing plies, of sidewalls, of beads, of protectors, of underlayers, of rubber blocks and other internal rubbers providing the interface between the abovementioned regions of the tires.

The term "isoprene elastomer" is understood to mean, in a known way, an isoprene homopolymer or copolymer, in other words a diene elastomer chosen from the group consisting of natural rubber (NR), synthetic polyisoprenes (IR), the various copolymers of isoprene and the mixtures of these elastomers. Mention will in particular be made, among isoprene copolymers, of isobutene/isoprene copolymers (butyl rubber—IIR), isoprene/stirene copolymers (SIR), isoprene/butadiene copolymers (BIR) or isoprene/butadiene/stirene copolymers (SBIR). This isoprene elastomer is preferably natural rubber or a synthetic cis-1,4-polyisoprene; use is preferably made, among these synthetic polyisoprenes, of the polyisoprenes having a level (molar %) of cis-1,4-bonds of greater than 90%, more preferably still of greater than 98%.

According to another specific embodiment, in particular when it is intended for a tire sidewall or for an airtight internal rubber of a tubeless tire (or other air-impermeable component), the composition in accordance with the invention can comprise at least one essentially saturated diene elastomer, in particular at least one EPDM copolymer or one butyl rubber (optionally chlorinated or brominated), whether these copolymers are used alone or as a mixture with highly unsaturated diene elastomers as mentioned above, in particular NR or IR, BR or SBR.

According to another preferred embodiment of the invention, the rubber composition comprises a blend of a (one or more) "high Tg" diene elastomer exhibiting a Tg of between −70° C. and 0° C. and of a (one or more) "low Tg" diene elastomer exhibiting a Tg of between −110° C. and −80° C., more preferably between −105° C. and −90° C. The high Tg elastomer is preferably chosen from the group consisting of S-SBRs, E-SBRs, natural rubber, synthetic polyisoprenes (exhibiting a level (molar %) of cis-1,4-structures preferably of greater than 95%), BIRs, SIRs, SBIRs and the mixtures of these elastomers. The low Tg elastomer preferably comprises butadiene units according to a level (molar %) at least equal to 70%; it preferably consists of a polybutadiene (BR) exhibiting a level (molar %) of cis-1,4-structures of greater than 90%.

According to another specific embodiment of the invention, the rubber composition comprises, for example, from 30 to 100 phr, in particular from 50 to 100 phr, of a high Tg elastomer as a blend with 0 to 70 phr, in particular from 0 to 50 phr, of a low Tg elastomer; according to another example, it comprises, for the whole of the 100 phr, one or more SBR(s) prepared in solution.

According to another specific embodiment of the invention, the diene elastomer of the composition according to the invention comprises a blend of a BR (as low Tg elastomer) exhibiting a level (molar %) of cis-1,4-structures of greater than 90% with one or more S-SBRs or E-SBRs (as high Tg elastomer(s)).

The composition according to the invention can comprise a single diene elastomer or a mixture of several diene elastomers, it being possible for the diene elastomer or elastomers to be used in combination with any type of synthetic elastomer other than a diene elastomer, indeed even with polymers other than elastomers, for example thermoplastic polymers.

II-2. Reinforcing Filler

Use may be made of any type of reinforcing filler known for its capabilities of reinforcing a rubber composition which can be used in the manufacture of tires, for example an organic filler, such as carbon black, a reinforcing inorganic filler, such as silica, or a blend of these two types of filler, in particular a blend of carbon black and silica.

All carbon blacks, in particular blacks of the HAF, ISAF or SAF type, conventionally used in tires ("tire-grade" blacks) are suitable as carbon blacks. Mention will more particularly be made, among the latter, of the reinforcing carbon blacks of the 100, 200 or 300 series (ASTM grades), such as, for example, the N115, N134, N234, N326, N330, N339, N347 or N375 blacks, or also, depending on the applications targeted, the blacks of higher series (for example, N660, N683 or N772). The carbon blacks might, for example, be already incorporated in the isoprene elastomer in the form of a masterbatch (see, for example, Applications WO 97/36724 or WO 99/16600).

Mention may be made, as examples of organic fillers other than carbon blacks, of the functionalized polyvinylaromatic organic fillers as described in Applications WO-A-2006/069792 and WO-A-2006/069793.

The term "reinforcing inorganic filler" should be understood, in the present patent application, by definition, as meaning any inorganic or mineral filler, whatever its colour and its origin (natural or synthetic), also known as "white filler", "clear filler" or even "non-black filler", in contrast to carbon black, capable of reinforcing by itself alone, without means other than an intermediate coupling agent, a rubber composition intended for the manufacture of tires, in other words capable of replacing, in its reinforcing role, a conventional tire-grade carbon black; such a filler is generally characterized, in a known way, by the presence of hydroxyl (—OH) groups at its surface.

The physical state under which the reinforcing inorganic filler is provided is not important, whether it is in the form of a powder, of microbeads, of granules, of beads or any other appropriate densified form. Of course, the term reinforcing inorganic filler is also understood to mean mixtures of different reinforcing inorganic fillers, in particular of highly dispersible siliceous and/or aluminous fillers as described below.

Mineral fillers of the siliceous type, in particular silica ($SiO_2$), or of the aluminous type, in particular alumina ($Al_2O_3$), are suitable in particular as reinforcing inorganic fillers. The silica used can be any reinforcing silica known to a person skilled in the art, in particular any precipitated or pyrogenic silica exhibiting a BET surface and a CTAB specific surface both of less than 450 $m^2/g$, preferably from 30 to 400 $m^2/g$. Mention will be made, as highly dispersible ("HDS") precipitated silicas, for example, of the Ultrasil 7000 and Ultrasil 7005 silicas from Degussa, the Zeosil 1165MP, 1135MP and 1115MP silicas from Rhodia, the Hi-Sil EZ150G silica from PPG, the Zeopol 8715, 8745 and 8755 silicas from Huber or the silicas with a high specific surface as described in Application WO 03/16837.

When the composition according to the invention is intended for tire treads having a low rolling resistance, the reinforcing inorganic filler used, in particular if it is silica, preferably has a BET surface of between 45 and 400 $m^2/g$, more preferably of between 60 and 300 $m^2/g$.

Preferably, the level of total reinforcing filler (carbon black and/or reinforcing inorganic filler, such as silica) is between 20 and 200 phr, more preferably between 30 and 150 phr, the optimum being in a known way different depending on the specific applications targeted: the level of reinforcement expected with regard to a bicycle tire, for example, is, of course, less than that required with regard to a tire capable of running at high speed in a sustained manner, for example a motorcycle tire, a tire for a passenger vehicle or a tire for a utility vehicle, such as a heavy duty vehicle.

According to a preferred embodiment of the invention, use is made of a reinforcing filler comprising between 30 and 150 phr, more preferably between 50 and 120 phr, of inorganic filler, particularly silica, and optionally carbon black; the carbon black, when it is present, is preferably used at a level of less than 20 phr, more preferably of less than 10 phr (for example, between 0.1 and 10 phr).

In order to couple the reinforcing inorganic filler to the diene elastomer, use is made, in a known way, of an at least bifunctional coupling agent (or bonding agent) intended to provide a satisfactory connection, of chemical and/or physical nature, between the inorganic filler (surface of its particles) and the diene elastomer, in particular bifunctional organosilanes or polyorganosiloxanes.

Use is made in particular of silane polysulphides, referred to as "symmetrical" or "unsymmetrical" depending on their specific structure, as described, for example, in Applications WO 03/002648 (or US 2005/016651) and WO 03/002649 (or US 2005/016650).

"Symmetrical" silane polysulphides corresponding to the following general formula (III):

$$Z\text{-}A\text{-}S_x\text{-}A\text{-}Z, \text{ in which:} \tag{III}$$

x is an integer from 2 to 8 (preferably from 2 to 5);
A is a divalent hydrocarbon radical (preferably, $C_1$-$C_{18}$ alkylene groups or $C_6$-$C_{12}$ arylene groups, more particularly $C_1$-$C_{10}$, in particular $C_1$-$C_4$, alkylenes, especially propylene);
Z corresponds to one of the formulae below:

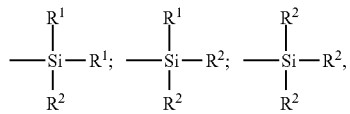

in which:
the $R^1$ radicals, which are unsubstituted or substituted and identical to or different from one another, represent a $C_1$-$C_{18}$ alkyl, $C_5$-$C_{18}$ cycloalkyl or $C_6$-$C_{18}$ aryl group (preferably, $C_1$-$C_6$ alkyl, cyclohexyl or phenyl groups, in particular $C_1$-$C_4$ alkyl groups, more particularly methyl and/or ethyl),
the $R^2$ radicals, which are unsubstituted or substituted and identical to or different from one another, represent a $C_1$-$C_{18}$ alkoxyl or $C_5$-$C_{18}$ cycloalkoxyl group (preferably a group chosen from $C_1$-$C_8$ alkoxyls and $C_5$-$C_8$ cycloalkoxyls, more preferably still a group chosen from $C_1$-$C_4$ alkoxyls, in particular methoxyl and ethoxyl), are suitable in particular, without the above definition being limiting.

In the case of a mixture of alkoxysilane polysulphides corresponding to the above formula (III), in particular the usual mixtures available commercially, the mean value of the "x" index is a fractional number preferably of between 2 and 5, more preferably in the vicinity of 4. However, the invention can also advantageously be carried out, for example, with alkoxysilane disulphides (x=2).

Mention will more particularly be made, as examples of silane polysulphides, of bis(($C_1$-$C_4$)alkoxyl($C_1$-$C_4$)alkylsilyl ($C_1$-$C_4$)alkyl) polysulphides (in particular disulphides, trisulphides or tetrasulphides), such as, for example, bis(3-trimethoxysilylpropyl) or bis(3-triethoxysilylpropyl) polysulphides. Use is in particular made, among these compounds, of bis(3-triethoxysilylpropyl) tetrasulphide, abbreviated to TESPT, of formula $[(C_2H_5O)_3Si(CH_2)_3S_2]_2$, or bis (triethoxysilylpropyl) disulphide, abbreviated to TESPD, of formula $[(C_2H_5O)_3Si(CH_2)_3S]_2$. Mention will also be made, as preferred examples, of bis(mono($C_1$-$C_4$) alkoxyldi ($C_1$-$C_4$) alkylsilylpropyl) polysulphides (in particular disulphides, trisulphides or tetrasulphides), more particularly bis (monoethoxydimethylsilylpropyl) tetrasulphide, as described in Patent Application WO 02/083782 (or US 2004/132880).

Mention will in particular be made, as coupling agent other than alkoxysilane polysulphide, of bifunctional POSs (polyorganosiloxanes) or of hydroxysilane polysulphides ($R^2$=OH in the above formula III), such as described in Patent Applications WO 02/30939 (or U.S. Pat. No. 6,774,255) and WO 02/31041 (or US 2004/051210), or of silanes or POSs carrying azodicarbonyl functional groups, such as described, for example, in Patent Applications WO 2006/125532, WO 2006/125533 and WO 2006/125534.

In the rubber compositions in accordance with the invention, the content of coupling agent is preferably between 4 and 12 phr, more preferably between 3 and 8 phr.

A person skilled in the art will understand that a reinforcing filler of another nature, in particular organic nature, might be used as filler equivalent to the reinforcing inorganic filler described in the present section, provided that this reinforcing filler is covered with an inorganic layer, such as silica, or else comprises, at its surface, functional sites, in particular hydroxyls, requiring the use of a coupling agent in order to form the connection between the filler and the elastomer.

II.3 Vulcanization System

The vulcanization system proper is based on sulphur (or on a sulphur-donating agent) and on a primary vulcanization accelerator. Additional to this base vulcanization system are various known secondary vulcanization accelerators or vulcanization activators, such as zinc oxide, stearic acid or equivalent compounds, or guanidine derivatives (in particular diphenylguanidine), incorporated during the first non-productive phase and/or during the productive phase, as described subsequently.

The sulphur is used at a preferred level of between 0.5 and 10 phr, more preferably of between 0.5 and 5 phr, in particular between 0.5 and 3 phr, when the composition of the invention is intended, according to a preferred form of the invention, to constitute a tire tread.

The primary vulcanization accelerator must make possible crosslinking of the rubber compositions within industrially acceptable times, while retaining a minimum safety period ("scorch time") during which the compositions can be shaped without the risk of premature vulcanization ("scorching").

According to the invention, the vulcanization system comprises, as primary vulcanization accelerator, one or more 1,2,4-triazine compounds of formula:

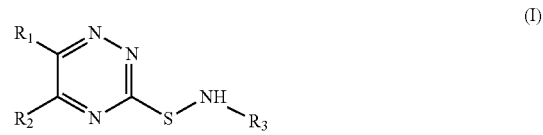

where
$R_1$ and $R_2$ independently represent H or a $C_1$-$C_{25}$-hydrocarbon group chosen from linear, branched or cyclic alkyl groups and aryl groups, optionally interrupted by one or more heteroatoms, it being possible for $R_1$ and $R_2$ to together form a ring,
$R_3$ represents:
a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

The compounds of formula (I) can advantageously replace, in all or part, the sulphenamide compounds conventionally used.

The term cyclic alkyl group is understood to mean an alkyl group composed of one or more rings.

The heteroatom or heteroatoms can be a nitrogen, sulphur or oxygen atom.

$R_1$ and $R_2$ can independently represent H, a methyl group or a phenyl group.

Advantageously, $R_1$ or $R_2$ represents a phenyl group. Preferably, $R_2$ is a phenyl group and $R_1$ is a hydrogen.

Advantageously, $R_3$ represents a cyclohexyl group or a tert-butyl group.

Preferably, $R_3$ represents a cyclohexyl group.

Thus, a preferred compound of formula (I) is that in which $R_1$ represents H, $R_2$ represents a phenyl group and $R_3$ represents a cyclohexyl. In this case, the triazine compound of formula (I) is 3-[(cyclohexylamino)thio]-5-phenyl-1,2,4-triazine.

According to another preferred embodiment, $R_3$ represents a tert-butyl group.

Thus, another preferred compound (I) is that in which $R_1$ represents hydrogen, $R_2$ represents a phenyl group and $R_3$ represents a tert-butyl group. Such a compound is 3-[(t-butylamino)thio]-5-phenyl-1,2,4-triazine.

The compound or compounds of formula (I) generally represent from 0.1 to 10 phr, preferably from 0.5 to 7 phr and better still from 0.5 to 5 phr (parts by weight per hundred of diene elastomer).

The 1,2,4-triazine compound or compounds present in the composition according to the invention can be prepared according to the process comprising the following stages:

the starting material is the compound (A) of following formula:

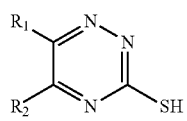

(A)

where $R_1$ and $R_2$ are as defined above, it being possible for this 1,2,4-triazine-3-thiol to be obtained, without this being limiting, by condensation between a 1,2-dicarbonyl compound and thiosemicarbazide according to generic methods described, for example, in the Journal of Organic Chemistry, Vol. 52, No. 19, 1987, pp. 4280-4287, or by L. M. Mironovich and V. K. Promonenkov in the chapter entitled 1,2,4-Triazines of Volume 22 of the work Progress in Science and Technology, Organic Chemistry Series, published in 1990 by Viniti in Moscow;

compound (A) is reacted with a basic composition which can be an aqueous solution of an organic or inorganic base, for example an aqueous sodium hydroxide solution, then a primary amine of formula $R_3NH_2$, where $R_3$ is as defined above, is added to the reaction medium and an oxidative coupling is carried out in the presence of an oxidizing compound, which can, for example, be a halogen compound, such as chlorine, bromine or iodine, or hypohalous acids or their alkali metal salts, such as, for example, sodium hypochlorite.

Preferably, $R_1$ represents hydrogen and $R_2$ represents a phenyl group.

Preferably, $R_3$ represents a cyclohexyl group.

The 1,2,4-triazine compound or compounds of formula (I) present in the composition according to the invention can also be prepared according to a synthetic process comprising the following stages:

a) primary amine of formula $R_3NH_2$, where $R_3$ is defined as above, is reacted with an oxidizing compound, then b) a composition comprising a basic composition, primary amine of formula $R_3NH_2$ and a compound of following formula (A):

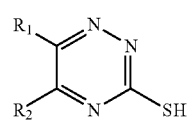

(A)

where $R_1$ and $R_2$ are as defined above,
it being possible for this compound to be obtained as indicated above,
is added to the reaction medium obtained in stage a).

Preferably, $R_1$ represents hydrogen and $R_2$ represents a phenyl group.

Preferably, $R_3$ represents a tert-butyl group.

The basic composition can be an aqueous solution of an organic or inorganic base, for example an aqueous sodium hydroxide solution.

The oxidizing compound can be chosen from halogen compounds, preferably chlorine, bromine or iodine, and hypohalous acids and their alkali metal salts. Mention may in particular be made of sodium hypochlorite.

The vulcanization system of the composition according to the invention can also comprise one or more additional primary accelerators, in particular the compounds of the family of the thiurams, zinc dithiocarbamate derivatives or thiophosphates.

II-4. Various Additives

The rubber composition according to the invention can also comprise all or a portion of the normal additives generally used in elastomer compositions intended for the manufacture of tires, in particular treads, such as, for example, plasticizing agents or extending oils, whether the latter are aromatic or non-aromatic in nature, pigments, protection agents, such as antiozone waxes (such as Cire Ozone C32 ST), chemical antiozonants, antioxidants (such as N-(1,3-dimethylbutyl)-N'-phenyl-p-phenylenediamine), antifatigue agents, reinforcing resins, methylene acceptors (for example, novolac phenolic resin) or methylene donors (for example, HMT or H3M), such as described, for example, in Application WO 02/10269.

Preferably, the composition according to the invention comprises, as preferred non-aromatic or very slightly aromatic plasticizing agent, at least one compound chosen from the group consisting of naphthenic oils, paraffinic oils, MES oils, TDAE oils, glycerol esters (in particular trioleates), plasticizing hydrocarbon resins exhibiting a high Tg preferably of greater than 30° C., and the mixtures of such compounds.

The composition according to the invention can also comprise, in addition to the coupling agents, coupling activators for the reinforcing inorganic filler or more generally processing aids capable, in a known way, by virtue of an improvement in the dispersion of the inorganic filler in the rubber matrix and of a lowering in the viscosity of the compositions, of improving their property of processing in the raw state, these agents being, for example, hydrolysable silanes, such as alkylalkoxysilanes (in particular alkyltriethoxy-silanes), polyols, polyethers (for example, polyethylene glycols), primary, secondary or tertiary amines (for example, trialkanolamines), hydroxylated or hydrolysable POSs, for example α,ω-dihydroxypolyorgano-siloxanes (in particular α,ω-dihydroxypolydimethyl-siloxanes), or fatty acids, such as, for example, stearic acid.

II-5. Manufacture of the Rubber Compositions

The rubber composition according to the invention is manufactured in appropriate mixers using two successive preparation phases according to a general procedure well known to a person skilled in the art: a first phase of thermomechanical working or kneading (sometimes described as "non-productive" phase) at high temperature, up to a maximum temperature of between 130° C. and 200° C., preferably between 145° C. and 185° C., followed by a second phase of mechanical working (sometimes described as "productive" phase) at a lower temperature, typically less than 120° C., for example between 60° C. and 100° C., finishing phase during which the crosslinking or vulcanization system is incorporated.

According to a preferred embodiment of the invention, all the base constituents of the composition of the invention, with the exception of the vulcanization system, namely the reinforcing filler or fillers and the coupling agent, if appropriate, are intimately incorporated, by kneading, in the diene elastomer or in the diene elastomers during the first "non-productive" phase, that is to say that at least these various base constituents are introduced into the mixer and are thermomechanically kneaded, in a single stage or several stages, until the maximum temperature of between 130° C. and 200° C., preferably of between 145° C. and 185° C., is reached.

By way of example, the first (non-productive) phase is carried out in a single thermomechanical stage during which all the necessary constituents, the optional additional processing aids and various other additives, with the exception of the vulcanization system, are introduced into an appropriate mixer, such as a normal internal mixer. The total duration of the kneading, in this non-productive phase, is preferably between 1 and 15 min. After cooling the mixture thus obtained during the first non-productive phase, the vulcanization system is then incorporated at low temperature, generally in an external mixer, such as an open mill; everything is then mixed (productive phase) for a few minutes, for example between 2 and 15 min.

The final composition thus obtained is subsequently calendered, for example in the form of a sheet or of a plaque, in particular for characterization in the laboratory, or also extruded in the form of a rubber profiled element which can be used, for example, as a tire tread for a passenger vehicle.

III. Examples of the Implementation of the Invention

III-1, 3-[(t-Butylamino)thio]-5-phenyl-1,2,4-triazine

A description is given here of the process for the preparation of 3-[(t-butylamino)thio]-5-phenyl-1,2,4-triazine (compound C) of following formula:

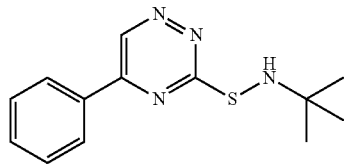 [SMILES: CC(C)(C)NSc1nncc(-c2ccccc2)n1]

The preparation of this sulfenamide is based on an oxidative coupling between 5-phenyl-1,2,4-triazine-3-thiol and tert-butylamine, according to the following synthetic scheme:

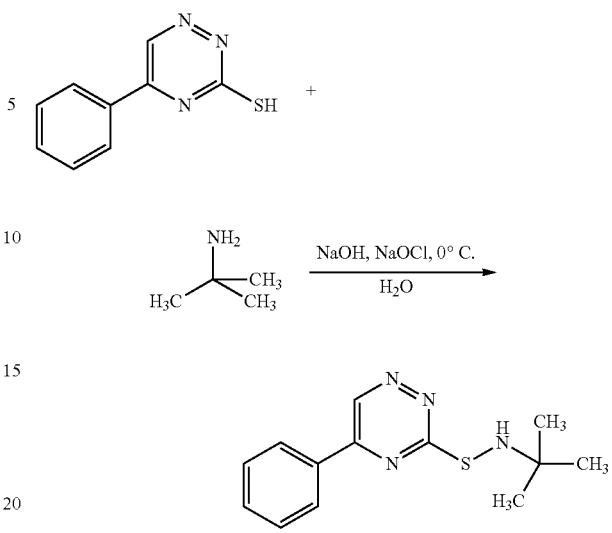

An aqueous NaOCl solution (136 ml, assayed at 17.4% active chlorine) is added dropwise over 45 min to 350 ml of tert-butylamine maintained between −10° C. and −5° C. (temperature of the bath). The temperature of the bath is maintained at between −10° C. and −5° C. throughout the duration of the addition. A solution of 5-phenyl-1,2,4-triazine-3-thiol (40.30 g, 0.213 mol; purity: approximately 98 molar %, determined by NMR), sodium hydroxide (16.96 g, 0.424 mol) and tert-butylamine (50 ml) in water (350 ml) is added dropwise over 90 min to this solution maintained at 0° C. The temperature of the reaction medium remains maintained between 0 and +6° C. The reaction medium is subsequently stirred at a temperature between +5° C. and +10° C. for one hour and then at ambient temperature for 2 hours.

Subsequently, this medium is diluted with 0.7 l of cold water (approximately 4° C.). This suspension is again stirred for 10 minutes and then the precipitate of the product obtained is filtered off, washed on the filter with water (10 times 500 ml) and then dried under air for 48 h. A yellow solid (49.5 g, 0.190 mol, yield 89%) with a melting point of 73° C. is obtained. The molar purity, determined by $^1$H NMR, is 95%.

The reaction is monitored by thin layer chromatography:

$Rf_{product}$=0.52, $Rf_{disulfide\ impurity}$=0.61 (characteristics of the TLC: $SiO_2$; EtOAc:heptane=1:1; visualization by UV and $I_2$).

The product is completely characterized by NMR. The chemical shifts obtained by $^1$H and $^{13}$C NMR in $d_6$-DMSO are given in the table below. Calibration is carried out with regard to DMSO (2.44 ppm in $^1$H and 39.5 ppm in $^{13}$C).

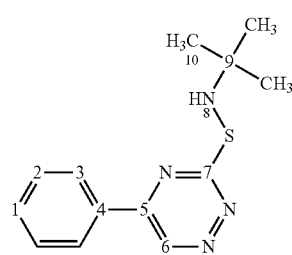

The results are given in Table 1.

TABLE 1

| | No. | | | | | | | | | |
|---|---|---|---|---|---|---|---|---|---|---|
| | 1 | 2 | 3 | 4 | 5 | 6 | 7 | 8 | 9 | 10 |
| δ $^1$H ppm | 7.59 | 7.56 | 8.29 | — | — | 9.72 | — | 4.87 | — | 1.11 |
| δ $^{13}$C ppm | 132.7 | 128.9 | 127.7 | 129.7 | 153.7 | 142.9 | 177.0 | — | 54.3 | 29.1 |

III-2. 3-[(Cyclohexylamino)thio]-5-phenyl-1,2,4-triazine

In the following examples, the invention is implemented with 3-[(cyclohexylamino)thio]-5-phenyl-1,2,4-triazine (compound B) of following formula:

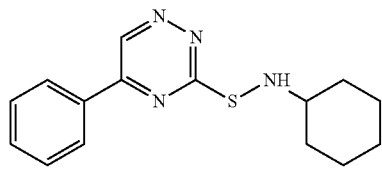 [SMILES: c1ccc(-c2cnnc(SNC3CCCCC3)n2)cc1]

III-2.1. Synthesis of Triazine Compound B

This compound is prepared from 5-phenyl-1,2,4-triazine-3-thiol and cyclohexylamine according to the following synthetic scheme:

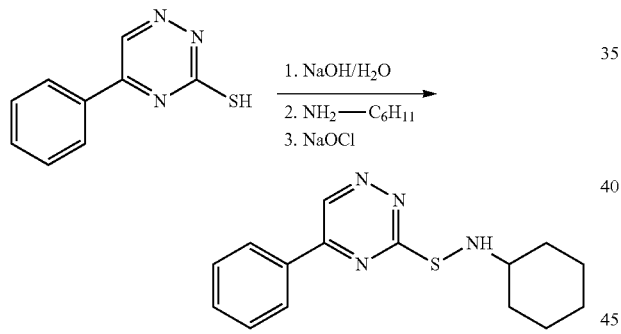

5-Phenyl-1,2,4-triazine-3-thiol (CAS number [15969-28-5]) is commercially available and can be obtained according to procedures described in the following documents:

1. Daunis, J. et al.; Bulletin de la Societe Chimique de France, 1969, 10, 3675-3678.
2. Joshi, Krishna C., Dubey, Kalpana and Dandia, Anshu, Heterocycles, 1981 16, 9, 1545-1553.

Cyclohexylamine (107.6 g, 1.09 mol) is added to a solution of 5-phenyl-1,2,4-triazine-3-thiol (41.0 g, 0.22 mol) and sodium hydroxide (20.0 g, 0.50 mol) in H$_2$O (700 ml). The mixture is cooled down to a temperature of between 0 and −5° C. and then the aqueous NaOCl solution (4% active chlorine) (477 ml) is added dropwise over 30 minutes. The temperature of the reaction medium remains between 0 and −4° C. The reaction medium is subsequently stirred at a temperature of between 0 and 5° C. for from 1 h 30 to 2 hours.

Petroleum ether (100 ml, 40/60° C. fraction) is added and the reaction medium is subsequently stirred at a temperature of between 0 and −4° C. for from 15 to 30 minutes. The precipitate is filtered off, washed on the filter with water (200 ml) and petroleum ether (50 ml, 40/60° C. fraction) and finally dried under reduced pressure for from 2 to 3 hours.

A white solid (42.9 g, 0.15 mol, yield 68%) with a melting point of 125-127° C. is obtained.

The molar purity is greater than 97% ($^1$H NMR).

If the purity is inadequate, crystallization from ethyl acetate makes it possible to obtain the pure product.

The product is completely characterized by NMR. The chemical shifts obtained by $^1$H and $^{13}$C NMR in d$_6$-DMSO are given in the table below. Calibration is carried out with regard to DMSO (2.44 ppm in $^1$H and 39.5 ppm in $^{13}$C).

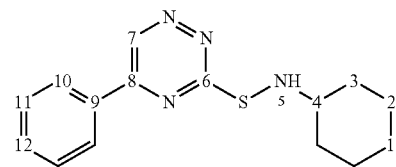

The results are shown in Table 2.

TABLE 2

| | No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| δ ($^1$H) in ppm | 1.45 1.13 | 1.63 1.13 | 1.92 1.13 | 2.97 | 5.08 | / | 9.73 | / | / | 8.27 | 7.56 | 7.61 |
| δ ($^{13}$C) in ppm | 25.5 | 23.8 | 32.4 | 56.7 | / | 176.4 | 143.2 | 154.2 | 132.9 | 127.8 | 129.3 | 132.8 |

III-2.2. Preparation of the Compositions

The procedure for the tests which follow is as follows: the diene elastomer or elastomers, the reinforcing filler or fillers and the optional coupling agent, followed, after kneading for one to two minutes, by the various other ingredients, with the exception of the vulcanization system, are introduced into an internal mixer, 70% filled and having a starting vessel temperature of approximately 90° C. Thermomechanical working (non-productive phase) is then carried out in one stage (total duration of the kneading equal to approximately 5 min), until a maximum "dropping" temperature of approximately 165° C. is reached. The mixture thus obtained is recovered and cooled, and then the vulcanization system (sulphur and 1,2,4-triazine compound) is added on an external mixer (homofinisher) at 70° C., everything being mixed (productive phase) for approximately 5 to 6 min.

The compositions thus obtained are subsequently calendered, either in the form of plaques (thickness of 2 to 3 mm) or of thin sheets of rubber, for the measurement of their physical or mechanical properties, or in the form of profiled elements which can be used directly, after cutting out and/or assembling to the desired dimensions, for example as semi-finished products for tires, in particular as tire treads.

III-2.3 Characterization Tests—Results

A—Example 1

The object of this example is to compare the properties of a rubber composition comprising carbon black as predominant reinforcing filler, which can be used in the manufacture of a tire tread, comprising 3-[(cyclohexylamino)thio]-5-phenyl-1,2,4-triazine (compound B) as primary vulcanization accelerator (composition 2), with the properties of a rubber composition comprising N-cyclohexyl-2-benzothiazole-sulphenamide ("CBS") (composition 1).

The formulations of the compositions are given in Table 3. The amounts are expressed as parts per 100 parts by weight of elastomer (phr).

TABLE 3

|  | Composition 1 | Composition 2 |
| --- | --- | --- |
| NR (1) | 40 | 40 |
| BR (2) | 20 | 20 |
| SBR (3) | 40 | 40 |
| N234 (4) | 54 | 54 |
| Paraffin | 1 | 1 |
| 6-PPD (5) | 2 | 2 |
| Stearic acid | 2 | 2 |
| ZnO | 2.7 | 2.7 |
| Sulphur | 1.1 | 1.1 |
| Vulcanization accelerator | 1.1* | 1.23** |

*CBS ("Santocure CBS" from Flexsys)
**3-[(cyclohexylamino)thio]-5-phenyl-1,2,4-triazine
(1) Natural rubber
(2) Polybutadiene with 0.7% of 1,2-, 1.7% of trans-1,4- and 98% of cis-1,4- (Tg = −105° C.) (molar %)
(3) Butadiene/stirene copolymer SSBR (SBR prepared in solution) with 25% of stirene, 59% of 1,2-polybutadiene units and 20% of trans-1,4-polybutadiene units (Tg = −24° C.) (molar %); level expressed as dry SBR (SBR extended with 9% by weight of MES oil, i.e. a total of SSBR + oil equal to 76 phr)
(4) Carbon black
(5) Antioxidant 6-p-phenylenediamine Rubber composition 2 comprising 3-[(cyclohexylamino)thio]-5-phenyl-1,2,4-triazine is identical to composition 1, it being understood that CBS is replaced with an isomolar amount of 3-[(cyclohexylamino)thio]-5-phenyl-1,2,4-triazine.

The rheometric properties at 150° C. are given in Table 4.

TABLE 4

|  | Composition 1 (CBS) | Composition 2 (Compound B) |
| --- | --- | --- |
| Rheo. prop. (DIN) | 150° C. | |
| Δtorque (dN · m) | 8.5 | 8.7 |
| k (min$^{-1}$) | 0.416 | 0.353 |
| t$_0$ (min) | 6.0 | 8.6 |

The rheometric properties obtained for composition 2 comprising 3-[(cyclohexylamino)thio]-5-phenyl-1,2,4-triazine are equivalent to those obtained for composition 1 comprising CBS. It is even noted that the delay phase (induction period $t_0$) is longer in the case of composition 2 comprising 3-[(cyclohexylamino)thio]-5-phenyl-1,2,4-triazine, which is advantageous.

It is furthermore noted that compound B, and the compounds of formula (I) in general, advantageously replace, with regard to the environmental impact, sulfenamides having a mercaptobenzothiazole ring system, by not generating, in contrast to the latter, mercaptobenzothiazole on decomposing during the curing.

B—Example 2

The object of this example is to compare the properties of a rubber composition comprising silica as predominant reinforcing filler, which can be used in the manufacture of a tire tread, comprising 3-[(cyclohexylamino)thio]-5-phenyl-1,2,4-triazine (compound B) as primary vulcanization accelerator (composition 4), with the properties of a rubber composition comprising N-cyclohexyl-2-benzothiazolesulphenamide ("CBS") (composition 3).

The formulations of the compositions are given in Table 5. The amounts are expressed as parts per 100 parts by weight of elastomer (phr).

TABLE 5

|  | Composition 3 | Composition 4 |
| --- | --- | --- |
| BR (1) | 28 | 28 |
| SBR (2) | 79.2 | 79.2 |
| N234 (3) | 4 | 4 |
| Silica (4) | 82 | 82 |
| 6-PPD (5) | 1.9 | 1.9 |
| MES/HPD (6) | 4.8 | 4.8 |
| Ozone wax C32 ST (7) | 1.5 | 1.5 |
| Resin (8) | 20 | 20 |
| Liquid silane (9) | 6.56 | 6.56 |
| Stearic acid | 2 | 2 |
| DPG (10) | 1.54 | 1.54 |
| ZnO | 1.5 | 1.5 |
| Sulphur | 1.2 | 1.2 |
| Vulcanization accelerator | 1.9* | 2.12** |

*CBS ("Santocure CBS" from Flexsys)
**3-[(cyclohexylamino)thio]-5-phenyl-1,2,4-triazine
(1) Polybutadiene with 0.7% of 1,2-, 1.7% of trans-1,4- and 98% of cis-1,4- (Tg = −105° C.) (molar %)
(2) Butadiene/stirene copolymer SSBR (SBR prepared in solution) with 25% of stirene, 59% of 1,2-polybutadiene units and 20% of trans-1,4-polybutadiene units (Tg = −24° C.) (molar %); level expressed as dry SBR (SBR extended with 9% by weight of MES oil, i.e. a total of SSBR + oil equal to 76 phr)
(3) Carbon black
(4) Silica "Zeosil 1165MP" from Rhodia, "HDS" type (BET and CTAB: approximately 160 m$^2$/g);
(5) Antioxidant 6-p-phenylenediamine
(6) Plasticizing oil "Medium Extracted Solvates" (Catenex SNR from Shell)
(7) Antiozonant
(8) Aliphatic resin (C$_5$ pure) "Hikorez A-1100", sold by Kolon
(9) Coupling agent
(10) Diphenylguanidine (Perkacit DPG from Flexsys)

Rubber composition 4 comprising 3-[(cyclohexylamino)thio]-5-phenyl-1,2,4-triazine is identical to composition 3, it being understood that the CBS is replaced with an isomolar amount of 3-[(cyclohexyl-amino)thio]-5-phenyl-1,2,4-triazine.

The rheometric properties at 150° C. are given in Table 6.

TABLE 6

|  | Composition 3 (CBS) | Composition 4 (Compound B) |
|---|---|---|
| Rheo. prop. (DIN) | 150° C. | |
| Δtorque (dN · m) | 11.9 | 12.2 |
| k (min$^{-1}$) | 0.064 | 0.052 |
| t$_0$ (min) | 4.9 | 6.9 |

The rheometric properties obtained for composition 4 comprising 3-[(cyclohexylamino)thio]-5-phenyl-1,2,4-triazine are equivalent to those obtained for composition 3 comprising CBS. It is even noted that the delay phase (induction period t$_0$) is longer in the case of the composition comprising 3-[(cyclohexylamino)-thio]-5-phenyl-1,2,4-triazine, which is advantageous.

Comparable results can be obtained with 3-[(t-butylamino)thio]-5-phenyl-1,2,4-triazine.

In conclusion, the 1,2,4-triazine compounds of the invention, used as vulcanization accelerator in rubber compositions comprising one or more reinforcing fillers, make it possible to improve the delay phase (induction period t$_0$).

The invention claimed is:

1. A rubber composition for the manufacture of tires, based on one or more diene elastomers, on one or more reinforcing fillers and on a vulcanization system, wherein the vulcanization system comprises one or more 1,2,4-triazine compounds of formula:

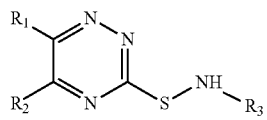

(I)

where

R$_1$ and R$_2$ independently represent H or a —C$_1$-C$_{25}$— hydrocarbon group chosen from linear, branched or cyclic alkyl groups and aryl groups, optionally interrupted by one or more heteroatoms, it being possible for R$_1$ and R$_2$ to together form a ring, R$_3$ represents:
a linear or branched —C$_1$-C$_{25}$— alkyl group which is optionally interrupted by one or more heteroatoms and which is optionally substituted by one or more cyclic —C$_3$-C$_{10}$— alkyl or —C$_6$-C$_{12}$— aryl groups, or
a cyclic —C$_3$-C$_{10}$— alkyl group which is optionally interrupted by one or more heteroatoms and which is optionally substituted by one or more linear, branched or cyclic —C$_1$-C$_{25}$— alkyl or —C$_6$-C$_{12}$— aryl groups which are optionally interrupted by one or more heteroatoms.

2. The composition according to claim 1, wherein R$_1$ and R$_2$ independently represent H, a methyl group or a phenyl group.

3. The composition according to claim 2, wherein R$_1$ or R$_2$ represents a phenyl group.

4. The composition according to claim 3, wherein R$_1$ represents a hydrogen and R$_2$ represents a phenyl group.

5. The composition according to claim 1, wherein R$_3$ represents a cyclohexyl group or a tert-butyl group.

6. The composition according to claim 1, wherein the 1,2,4-triazine compound or compounds represent from 0.1 to 10 phr.

7. The composition according to claim 1, wherein the diene elastomer or elastomers are chosen from the group consisting of polybutadienes, natural rubber, synthetic polyisoprenes, butadiene copolymers, isoprene copolymers and the mixtures of these elastomers.

8. The composition according to claim 7, wherein the diene elastomer is a blend of natural rubber with a polybutadiene and a butadiene/styrene copolymer, or a blend of a polybutadiene and a butadiene/styrene copolymer.

9. The composition according to claim 1, wherein the reinforcing filler or fillers are chosen from silica, carbon black and their mixtures.

10. The composition according to claim 1, wherein the reinforcing filler or fillers are present at a level of between 20 and 200 phr.

11. A process for preparing a rubber composition for the manufacture of tires as defined in claim 1, comprising the steps of:
incorporating the reinforcing filler or fillers in the diene elastomer or elastomers, during a "non-productive" stage, everything being kneaded thermomechanically, in one or more goes, until a maximum temperature of between 130° C. and 200° C. is reached,
cooling the combined mixture to a temperature of less than 100° C.,
subsequently incorporating, a "productive" stage, the vulcanization system and then kneading everything up to a maximum temperature of less than 120° C.

12. Finished article or semi-finished product intended for a motor vehicle ground-contact system, comprising a composition according to claim 1.

13. Tire, comprising a rubber composition as defined in claim 1.

14. The composition according to claim 1, wherein the 1,2,4-triazine compound or compounds represent from 0.5 to 7 phr.

15. The composition according to claim 1, wherein the 1,2,4-triazine compound or compounds represent from 0.5 to 5 phr.

16. The composition according to claim 1, wherein the reinforcing filler or fillers are present at a level of between 30 and 150 phr.

* * * * *